US008083022B2

(12) United States Patent
Gommel et al.

(10) Patent No.: US 8,083,022 B2
(45) Date of Patent: Dec. 27, 2011

(54) RECEIVER SUPPORT AND EARMOLD FOR A HEARING DEVICE AS WELL AS USE OF A THERMOPLAST FOR MANUFACTURING AN EARMOLD

(75) Inventors: Uli Gommel, Erlangen (DE); Daniela Hertel, Erlangen (DE)

(73) Assignee: Siemens Medical Instruments Pte. Ltd., Singapore (SG)

( * ) Notice: Subject to any disclaimer, the term of this patent is extended or adjusted under 35 U.S.C. 154(b) by 0 days.

(21) Appl. No.: 12/622,453

(22) Filed: Nov. 20, 2009

(65) Prior Publication Data

US 2010/0139054 A1 Jun. 10, 2010

(30) Foreign Application Priority Data

Dec. 5, 2008 (DE) ........................ 10 2008 060 701

(51) Int. Cl.
*A61B 7/02* (2006.01)

(52) U.S. Cl. ........................................ 181/135

(58) Field of Classification Search .................. 181/135
See application file for complete search history.

(56) References Cited

U.S. PATENT DOCUMENTS

| | | | | | |
|---|---|---|---|---|---|
| 4,977,976 | A * | 12/1990 | Major | ........................ | 181/130 |
| 6,070,693 | A * | 6/2000 | Hamery | ........................ | 181/135 |
| 6,695,093 | B1 * | 2/2004 | Falco | ........................ | 181/135 |
| 2006/0159298 | A1 * | 7/2006 | von Dombrowski et al. | . | 381/330 |
| 2007/0202735 | A1 * | 8/2007 | Hanks | ........................ | 439/427 |
| 2009/0071487 | A1 * | 3/2009 | Keady | ........................ | 128/864 |

FOREIGN PATENT DOCUMENTS

DE 10333293 A1 3/2005

* cited by examiner

*Primary Examiner* — Forrest M Phillips

(57) ABSTRACT

The invention specifies a receiver support for snapping into an earmold with a spherical section and with a conical section, which is embodied on the end facing the earmold and which tapers towards the earmold. The earmold comprises an adapter element permanently arranged in the earmold, into which the receiver support is able to be detachably firmly inserted. The adapter element features a bead-shaped depression, with which the spherical section of the receiver support can form a positive fit, so that the receiver support is supported to allow tilting or deflection in the adapter element. The invention also specifies the use of a thermoplast with selected properties for the manufacturing of the adapter element. The advantage is the secure and durable snap-in connection between a receiver support and an earmold.

12 Claims, 2 Drawing Sheets

RECEIVER SUPPORT AND EARMOLD FOR A HEARING DEVICE AS WELL AS USE OF A THERMOPLAST FOR MANUFACTURING AN EARMOLD

CROSS REFERENCE TO RELATED APPLICATIONS

This application claims priority of German application No. 10 2008 060 701.0 filed Dec. 05, 2008, which is incorporated by reference herein in its entirety.

FIELD OF THE INVENTION

The invention relates to a receiver support for a hearing device, an in-ear receiver, an earmold for a hearing device and use of a thermoplast for manufacturing an earmold specified in the claims.

BACKGROUND OF THE INVENTION

With the behind-the-ear and in-the-ear hearing devices available on the market it is necessary as a rule to connect an earpiece tailored to the auditory canal of a hearing device wearer to an in-ear loudspeaker. There are different solutions for establishing a secure connection depending on the design of the earpiece.

For individually adapted earpieces, also called earmolds, a mold of the wearer's ear is taken and in accordance with this mold a shell or a body is produced in rigid or hard version. The hard version is typically an otoplastic or a plastic shell produced by means of rapid prototyping technology. In these cases a "hard snap-in connection" is selected as the mechanical connection between loudspeaker, also referred to as receiver, and earpiece. FIG. 1 shows a schematic diagram of this "hard-hard connection". A spherically-shaped hard snap-in element 21 of a loudspeaker 23 can be introduced into an opening 22 of a hard earpiece 24 to form a precise fit. The undercut of the spherically-shaped hard snap-in element 21 means that the snap-in element 21 latches securely into the opening 22. Because of the hardness of the materials the connection elements 21, 22 must be embodied relatively small.

In another solution the earpieces are not individually adapted, but the hearing aid user can select from a limited number of different-sized, flexible earpieces made from a soft material, for example silicone. Different softnesses of earpiece cover the different auditory canal shapes of the hearing aid wearers. Since the respective earpiece does not fit the respective auditory canal exactly, the earpiece is commonly deformed reversibly on insertion into the auditory canal. It must therefore be designed to be as elastic as possible, in order to give a pleasant feeling when being worn. On the other hand the plug-in connection to the loudspeaker must be sufficiently firm to ensure that it is retained securely in the earpiece. This requires a minimum size of loudspeaker snap-in element. FIG. 2 shows this so-called "hard-soft connection" schematically. A spherically-shaped hard snap-in element 21 of a loudspeaker 23 can be introduced into an opening 22 of a soft earpiece 24 to form a precise fit by deforming the latter. Because of the different hardness of the materials the connection elements 21, 22 must be embodied relatively large to hold securely.

A further disadvantage of the "hard-soft connection" is that it can result in wear to the soft material from snapping it onto the hard material. The geometry of the snap-in element must however be designed "aggressively" so as to provide a secure hold. Thus the snap-in connection can no longer hold reliably after a small number of plug-in cycles.

The subsequently-published DE 10 2008 036 258 A1 specifies an earmold for a hearing device with an opening for accepting a snap-in element arranged on a receiver or on a sound tube, with the opening being lined with a hard layer. This offers the advantage of the connection being suitable both for soft and also for hard earmolds. Preferably the snap-in element is embodied in the shape of a sphere. This allows the snap-in element to be embodied very small.

SUMMARY OF THE INVENTION

The object of the invention is to specify an improved earmold and an improved snap-in element.

In accordance with the invention the desired object is achieved with the receiver support, with an in-ear receiver, with the earmold for a receiver and with the use of a thermoplast for manufacturing an earmold of the claims.

The invention claims a receiver support for snapping into an earmold with a spherical section and with a conical section which is embodied on the end facing towards the earmold and which tapers towards the earmold. This offers the advantage of a movable and still secure retention of the receiver support in an earmold.

In a further development the conical section is embodied such that when the receiver support tilts in the earmold it forms a stop. This enables the tilting or the defection of the receiver support to be restricted.

In a further embodiment the receiver support can be embodied rotation-symmetrically. The advantage is the ease of manufacturing.

Furthermore an axial and rotation-symmetrically-arranged sound channel can be embodied in the receiver support. The sound waves of a receiver reach a user's eardrum through this channel.

In addition the receiver support can be formed in one piece from a metal or from a hard plastic and be able to be welded or glued to a receiver. This offers a more secure connection to the receiver.

In a further inventive embodiment the receiver support can feature rotation-symmetrically arranged slits in the spherical section, through the form and number of which a force with which it is pushed into the earmold can be set. This offers the advantage of the insertion force being able to be determined exactly.

The invention also specifies an in-ear receiver for a hearing device with an inventive receiver support.

The invention also specifies an earmold for a hearing device that comprises an adapter element arranged firmly in the earmold, into which an inventive receiver support can be detachably firmly inserted. The adapter element features a bead-shaped depression running around the circumference of the inner side, with which the spherical section of the receiver support can form a positive fit, so that the receiver support is able to be tilted or deflected in the adapter element. The advantage of this is that a receiver support can snap securely into an earmold, is supported there to allow movement and can be removed from it again where necessary.

In a further embodiment the adapter element can be embodied as part of an opening of the earmold. This connects the adapter element firmly to the earmold.

In a development the earmold can be foiled from a soft, flexible plastic.

In a development the adapter element can be made of metal or formed from a hard plastic. This enables a hard-hard connection to be established between an earmold and a receiver support.

Furthermore the earmold can be produced using a two-component injection molding method from LSR/TPE and a thermoplast for the adapter element.

The invention also claims use of a thermoplast for manufacturing an inventive earmold with the following features:

Tensile elastic modulus as per ISO 527 with a test speed of 1 mm/min in the range 1000 to 3000 MPa, Elongation at yield stress as per ISO 527 ranging from 3 to 8%, Ball indentation hardness H358/30 ranging from 120 to 150 MPa and Separation force as per DIN ISO 813 with a cohesion tear between adapter element and earmold under tensile stress greater than 8 N/mm.

With these characteristics a durable and secure snap-in connection can be formed.

In a development the thermoplast can be polyamide or polybutylenterephthalate. These thermoplasts provide the required properties for a durable snap-in connection.

BRIEF DESCRIPTION OF THE DRAWINGS

Further special features and advantages of the invention will be evident from the subsequent explanations of an exemplary embodiment which refers to schematic diagrams.

The Figures show.

DETAILED DESCRIPTION OF THE INVENTION

Figure 1:
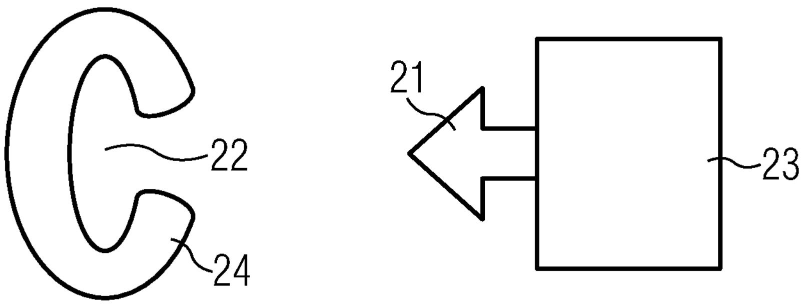
FIG 1 Prior Art
FIG. 1: a prior art snap-in connection between an earpiece and a loudspeaker.
Figure 2:
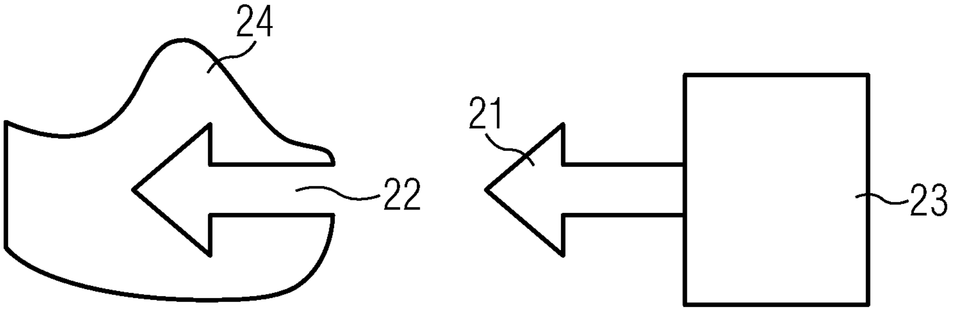
FIG 2 Prior Art
FIG. 2: a further prior art snap-in connection between an earpiece and a loudspeaker.
Figure 3:
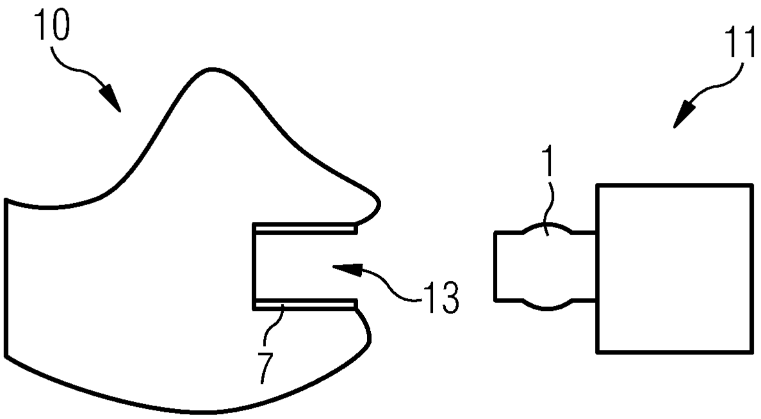
FIG. 3: an earmold and a receiver.
Figure 4:
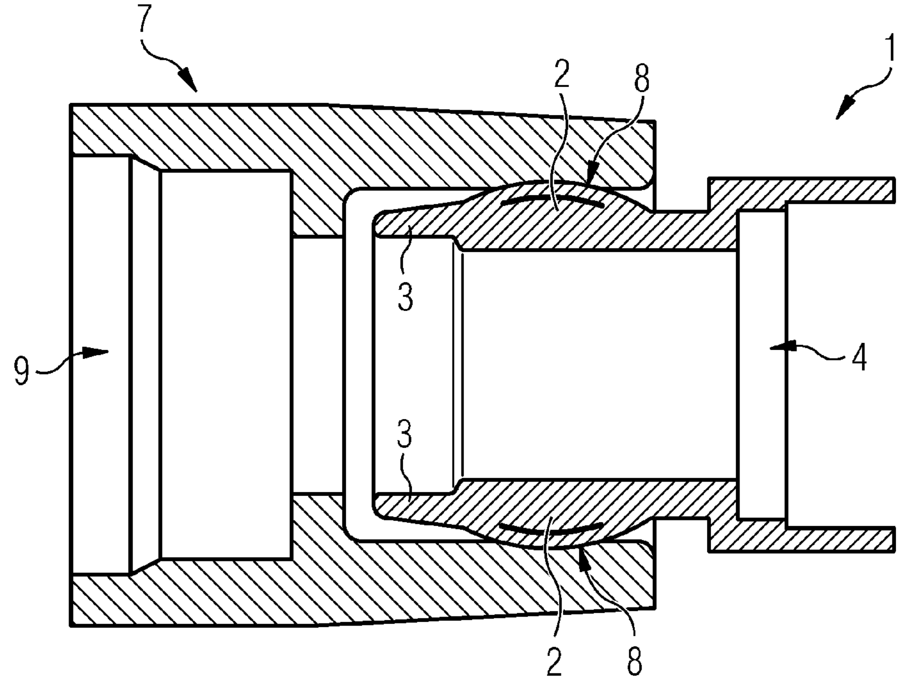
FIG. 4: a cross section through a receiver support snapped into an adapter element in the parallel position.
Figure 5:
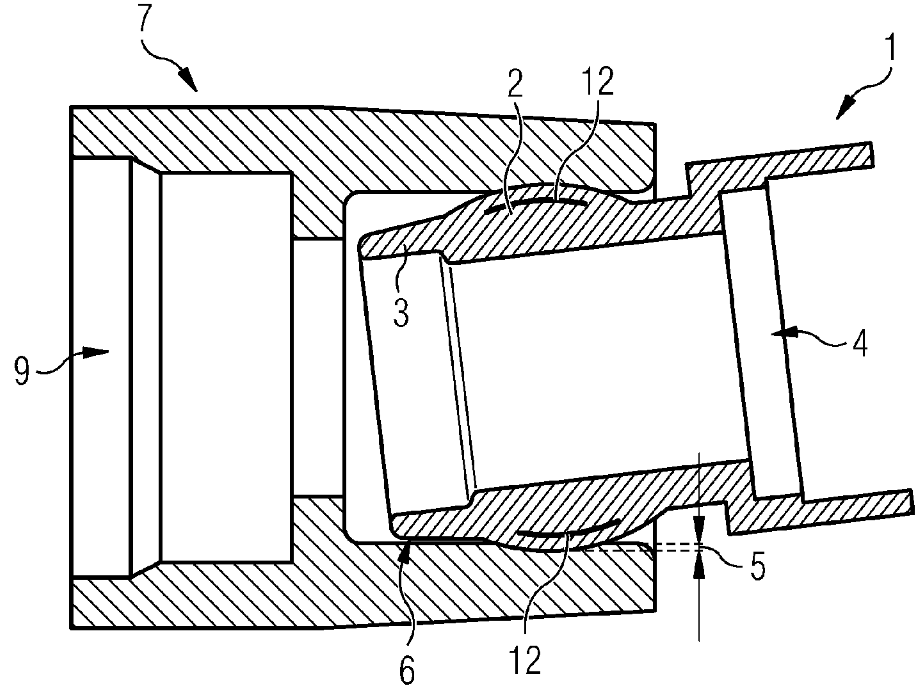
FIG. 5: a cross section through a receiver support snapped into an adapter element in the tilted position.

FIG. 3 shows an earmold 10 and a receiver 11. The earmold 10 features an opening 13 with an adapter element 7, into which the receiver support 1 attached to the receiver can snap. For a secure snap-in connection adapter element 7 and receiver support 1 must be suitably embodied. FIGS. 4 and 5 show the inventive solution in detail.

FIG. 4 shows a cross section through a receiver support 1 able to be connected to a receiver of a hearing device and through an adapter element 7 able to be connected to an earmold. For reasons of clarity the earmold is not shown in FIG. 4. The adapter element 7 is fitted into an opening of the earmold. Advantageously earmold and adapter element 7 are manufactured using a two-component injection molding method, with the adapter element 7 being formed from a hard thermoplast, such as Polyamide (PA) or Polybutylenterephthalate (PBT) for example. The thermoplast exhibits the following properties:

Tensile elastic modulus as per ISO 527 with a test speed of 1 mm/min in the range 1000 to 3000 MPa, Part-crystalline structure, Highest possible impact resistance as per ISO 179 1 eU, preferably without break, Elongation at yield stress as per ISO 527 ranging from 3 to 8%, Ball indentation hardness H358/30 ranging from 120 to 150 MPa and Separation force as per DIN ISO 813 with a cohesion tear between adapter element and eat mold under tensile stress greater than 8 N/mm.

The earmold is made from a soft material easily adaptable to the auditory canal, preferably from Liquid Silicone Rubber (LSR).

Alternately the earmold complete with adapter element 7 is formed in one piece from a hard plastic. The adapter element 7 can also be made of metal and pressed into the earmold.

The adapter element 7 is hollow with an opening 9 to allow the passage of sound waves and is preferably embodied in a cylindrical shape. The adapter element 7 accommodates the receiver support 1 in the form of a snap-in connection. To this end the receiver support 1 has a spherical section 2 which engages by a non-positive fit in a corresponding bead-shaped recess 8 of the adapter element 7. The spherical shape of the section 2 enables the receiver support 1 to be moved like a ball joint in the adapter element 7. The bead-shaped recess 8 or circumferential groove on the inner side of the adapter element 7 has a curvature that is approximately equal to the curvature of the spherical section 2 of the receiver support 1. FIG. 4 shows the receiver support 1 and the adapter element 7 aligned in a straight-ahead position in relation to one another.

FIG. 5 shows a cross section through the adapter element 7 and the receiver support 1 arranged in its opening 9 in accordance with FIG. 4 in a position tilted in relation to each other. Sound waves emitted by a receiver not shown reach the eardrum of a hearing device user via the sound channel 7 of the receiver support 1 and through an opening 9 in the adapter element 7. The spherical section 2 of the receiver support 2 snaps with a positive fit into a bead-shaped depression 8 of the adapter element 7 adapted to the radius of the spherical section 2. For a secure, but also detachable retention of the receiver support 1 in the adapter element 7 a rear grip 5 of around 0.02 to 0.10 mm is required. A maximum tilting of the receiver support 1 in the adapter element 7 is defined by the conical section 3. The receiver support 1 thus hits stop 6 with the adapter element 7. Depending on the shape of the conical section 3, the maximum tilt angle of the receiver support 1 can be adjusted. Theoretically any angles are possible. The conical section prevents an unintentional release of the push-in connection between receiver support 1 and adapter element 7 during excessive tilting or deflection of the receiver support 1. The conical section 3 also facilitates the introduction of the receiver support 1 into the adapter element 7.

As an alternative or also in addition to adjustment of the push-in force between receiver support 1 and adapter element 7 by the size of the undercut 5, the push-in force can also be adapted by making slits 12 in the spherical section 2 of the receiver support 1. The arrangement of the slits 12 is preferably rotation-symmetrical.

LIST OF REFERENCE SYMBOLS

1 Receiver support
2 Spherical section
3 Conical section
4 Sound channel in the receiver support 1
5 Rear grip between receiver support 1 and adapter element 7
6 Stop of the receiver support 1
7 Adapter element
8 Depression in the adapter element 7
9 Opening in the adapter element 7
10 Earmold

11 Receiver
12 Slit
13 Opening in the earmold 10
21 Snap-in element
22 Opening
23 Loudspeaker
24 Earpiece

The invention claimed is:

1. A receiver support of a hearing aid for snapping into an earmold comprising:

A spherical section; and

A conical section that is arranged on an end facing towards the earmold and tapers toward the earmold;

Wherein the earmold includes an adapter element with a circumferential and bead shaped user adjustable positive fit providing user adjustment of the tilt or deflection in the adapter element;

and wherein the conical section is configured to stop the receiver support when the receiver support is tilted in the earmold.

2. The receiver support as claimed in claim 1, wherein the receiver support is rotation-symmetrical.

3. The receiver support as claimed in claim 1, wherein a sound channel is arranged axially and rotation-symmetrically in the receiver support.

4. The receiver support as claimed in claim 1, wherein the receiver support is in one piece from a metal or a hard plastic and is able to be welded or glued to a receiver.

5. The receiver support as claimed in claim 1, wherein slits are arranged rotation-symmetrically in the spherical section and an insertion force can be set in the earmold through the slits.

6. An earmold for a hearing device comprising:

An adapter element arranged rigidly in the earmold that comprises a circumferential and bead-shaped depression; and a receiver support detachable rigidly inserted into the adapter element, the receiver support comprising:

A spherical section that forms a user adjustable positive fit providing user adjustment of tilt or deflection in the adapter element; and A conical section that is arranged on an end facing toward the earmold and tapers toward the earmold.

7. The earmold as claimed in claim 6, wherein the adapter element is a part of an opening of the earmold.

8. The earmold as claimed in claim 6, wherein the earmold is from a soft and flexible plastic.

9. The earmold as claimed in claim 6, wherein the adapter element is from a metal or a hard plastic.

10. The earmold as claimed in claim 6, wherein the earmold is manufactured from a two-component injection molding method from LSR/TPE and the adapter element is formed from a thermoplast.

11. A method for manufacturing an earmold for a hearing aid, comprising:

using a thermoplast for manufacturing the earmold, wherein the thermoplast comprises properties of:

tensile elastic modulus as per ISO 527 with a test speed of 1 mm/min in the range 1000 to 3000 MPa;

elongation at yield stress as per ISO 527 ranging from 3 to 8%;

ball indentation hardness H358/30 ranging from 120 to 150 MPa; and separation force as per DIN ISO 813 with a cohesion tear between an adapter element of the earmold and the earmold under a tensile stress greater than 8 N/mm.

12. The method as claimed in claim 11, wherein the thermoplast is a polyamide or a polybutylenterephthalate.

* * * * *